United States Patent [19]

Bohlen et al.

[11] Patent Number: 5,270,449
[45] Date of Patent: Dec. 14, 1993

[54] METHODS FOR THE ISOLATION OF HEPARIN-BINDING BRAIN MITOGENS

[75] Inventors: Peter Bohlen, Cortlandt, N.Y.; Peter Gautschi-Sova, Mellingen, Switzerland

[73] Assignee: American Cyanamid Company, Stamford, Conn.

[21] Appl. No.: 944,604

[22] Filed: Sep. 14, 1992

Related U.S. Application Data

[60] Division of Ser. No. 787,692, Nov. 1, 1991, Pat. No. 5,171,842, which is a continuation of Ser. No. 197,835, Jan. 25, 1988, abandoned.

[51] Int. Cl.$^5$ .................. C07K 15/08; C07K 3/18; C07K 3/22; C07K 3/28
[52] U.S. Cl. ..................... 530/350; 530/399; 530/413; 530/415; 530/416; 530/427
[58] Field of Search ............. 530/350, 399, 413, 416, 530/415, 427

[56] References Cited

PUBLICATIONS

Bohlen et al. 1984. Proc. Natl. Acad. Sci. 81:5364–5368.
Smith et al. 1984. Biochem Biophys. Res. Comm. 119(1):311–318.
Kato, Y. 1987. Adv. Chromatogr. 26:97–115.
Milner et al. 1989. Biochem. Biophys. Res. Comm. 165(3):1096–1103.
Merenmiér et al. 1990. J. Biol. Chem. 265(28):16721–16724.
Tezuka et al. 1990. Biochem Biophys. Res. Comm. 173(1):246–251.

Primary Examiner—Robert A. Wax
Assistant Examiner—Keith C. Furman
Attorney, Agent, or Firm—Alan M. Gordon

[57] ABSTRACT

A group of growth factors, designated heparin-binding brain mitogens (HBBMs), is disclosed. The HBBMs are isolated from brain tissue by a sequence of purification steps. The growth factors may be useful in the promotion of angiogenesis, such as in the promotion of wound healing, bone healing and in the treatment of burns, as well as in promoting the formation, maintenance and repair of tissue, in particular, neural tissue.

4 Claims, 7 Drawing Sheets

METHODS FOR THE ISOLATION OF HEPARIN-BINDING BRAIN MITOGENS

This is a divisional of co-pending application Ser. No. 07/787,692, filed on Nov. 1, 1991, U.S. Pat. No. 5,171,842, which is a continuation of application Ser. No. 07/147,835, filed on Jan. 25, 1988, now abandoned.

SUMMARY OF THE INVENTION

This invention relates to a group of novel protein growth factors which are believed to promote angiogenesis and, therefore, should be useful in wound healing, bone healing and the treatment of burns. The proteins induce mitogenesis in endothelial cells and, as such, may be considered to be growth factors for those cells. The proteins are also believed to promote the formation, maintenance and repair of tissue, in particular, neural tissue.

The proteins are isolated from brain cells and may each be termed a heparin-binding brain mitogen (HBBM). The proteins are single chain and highly basic. Three such proteins have been isolated from bovine brain, and have been designated HBBM-1, HBBM-2 and HBBM-3, with molecular weights of 18, 16 and 15 kd, respectively. The proteins possess a common 19 amino acid N-terminal sequence which differs from that of other known proteins.

The same three HBBMs have also been isolated from human brain tissue and have the same N-terminal sequence and the same type of mitogenic activity as bovine HBBMs. Rat and chicken brains have also been found to contain HBBMs.

The proteins are isolated and purified from brain tissue by a combination of steps, which include extraction from the tissue, heparin affinity chromatography, and cation-exchange chromatography. Hydrophobic interaction chromatography may be used as an auxiliary method of purification.

BACKGROUND OF THE INVENTION

Numerous protein growth factors have been isolated and characterized in recent years. These growth factors include epidermal growth factor, fibroblast growth factors, insulin-like growth factors, transforming growth factors, platelet-derived growth factor and interleukins. For example, fibroblast growth factor ("FGF") was first purified by Gospodarowicz in 1975 from bovine pituitary and had an estimated molecular weight of 13,300 daltons (Reference 1).

FGF was later purified from bovine brain (2). FGF can be isolated in either an acidic ("aFGF") or basic ("bFGF") form, depending on the isolation procedures used (3,4). A complete amino acid sequence for bovine pituitary bFGF (5) and bovine and human brain aFGF (6,7) has been published, together with the N-terminal sequences for bovine and human brain bFGF (5). The N-terminal sequences for bovine pituitary and bovine brain bFGF are identical (5,8).

It has now been found that, when the FGFs are purified from brain tissue using heparin-Sepharose affinity chromatography (9,10), a significant quantity of unknown proteins may also be present. Because proteins that bind with particularly high affinity to heparin are rare, further study of these unknown proteins was undertaken. This investigation revealed these proteins to be the HBBMs, which differ from the FGFs in their N-terminal sequence and amino acid compositions.

Accordingly, it is an object of this invention to isolate, purify and characterize the HBBMs from brain tissue. It is a further object of this invention to establish the physiological activity of the HBBMs.

DETAILED DESCRIPTION OF THE INVENTION

Figure 1:
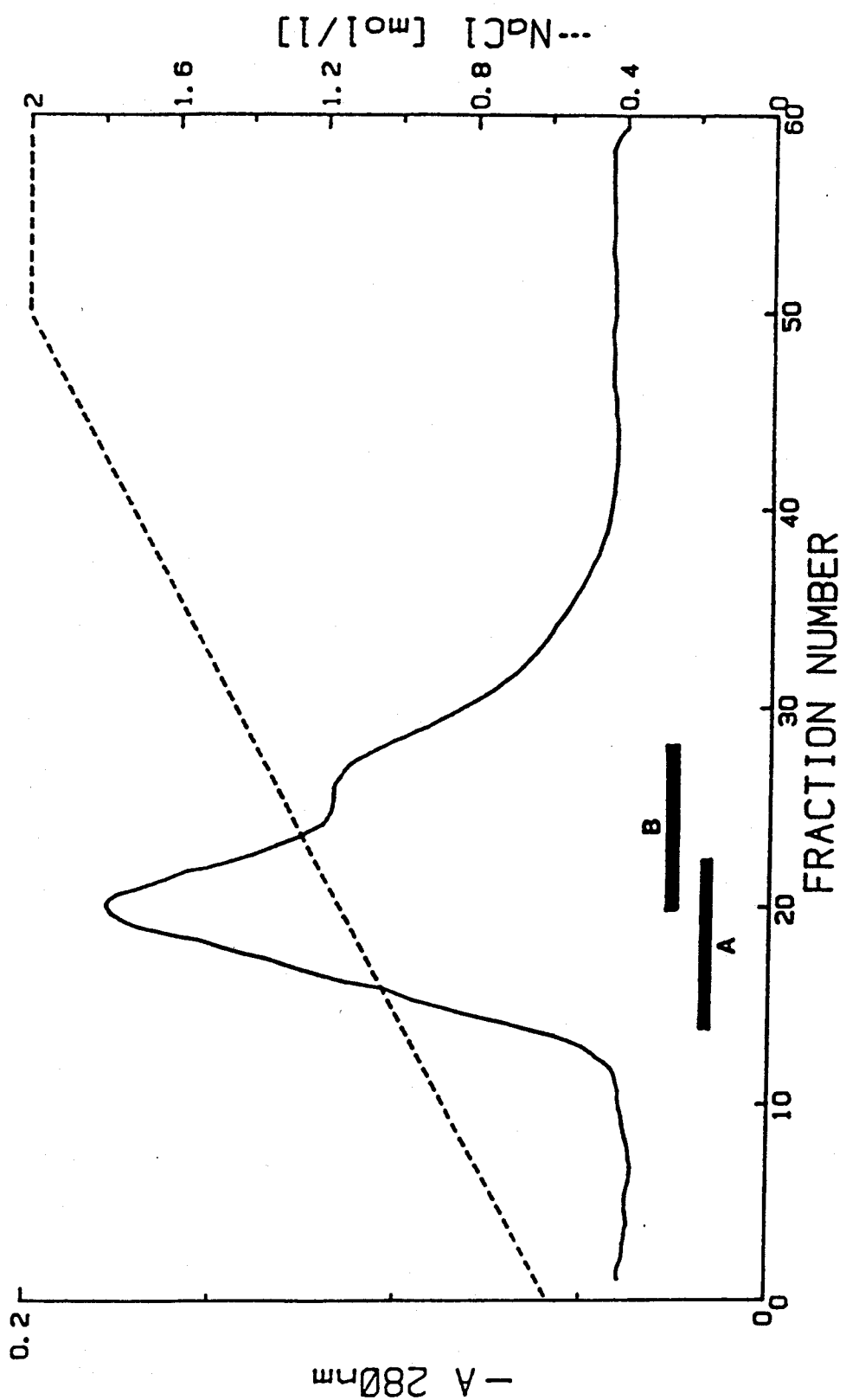
FIG. 1 depicts the fractionation of 400 ml of the 0.6M NaCl eluate from cation exchange chromatography using heparin-Sepharose affinity chromatography. The horizontal bar A indicates the fractions containing the HBBMs which were thereafter rechromatographed for further purifaction. The horizontal bar B indicates the fractions containing aFGF, as determined by reverse-phase HPLC analysis.

The novel growth factors of this invention are single chain, basic, heparin-binding brain mitogens. HBBMs have been identified in the brain tissues of all species tested, which include human, bovine, rat and chicken. Based on this distribution, it is expected that other species will also contain HBBMs.

The N-terminal sequences of the HBBMs differ markedly from those published for bovine or human brain aFGF and bFGF (5,6,7). The N-terminal sequences of the first 19 amino acids have been found to be identical for human and bovine HBBMs. The N-terminal sequences are as follows: Gly-Lys-Lys-Glu-Lys-Pro-Glu-Lys-Lys-Val-Lys-Lys-Ser-Asp-Cys-Gly-Glu-Trp-Gln. The rat sequence is identical with the exception of the cysteine residue in position 15, because a determination of the presence or absence of cysteine was not conducted. However, the fact that no other amino acid was identified at position 15 is consistent with the presumed presence of cysteine. To date, the first ten N-terminal residues of chicken HBBMs have been sequenced; they are identical to those of human, bovine and rat HBBMs.

The HBBMs have been found in three forms in tissue from bovine brain. HBBM-1, HBBM-2 and HBBM-3 have molecular weights of 18, 16 and 15 kD, respectively. Their amino acid compositions (determined as hereinafter described) are set forth in Table I below and also differ from the amino acid compositions of the bovine brain FGFs (5,6,7).

Based on the molecular weights and the identical N-terminal sequences, it is concluded that the three HBBMs probably differ at their C-termini. The available data strongly suggest that HBBM-2 and HBBM-3 are C-terminally truncated forms of HBBM-1, lacking approximately 13 and 29 amino acids, respectively.

It was found that the ratios of the three forms varied between different isolation batches. However, on average, based on quantitative amino acid analysis, the overall isolation yield of HBBMs was estimated at approximately 30, 10 and 40 $\mu$g/kg brain tissue for HBBM-1, HBBM-2, and HBBM-3, respectively. The ratios may depend on variables during tissue storage and extraction, in particular proteolysis. Proteolysis during tissue re-extraction may cause carboxy-terminal truncation of HBBM-1, the largest of the HBBM forms, which would yield HBBM-2 and HBBM-3 in varying amounts.

The process for isolating the novel HBBMs of this invention in substantially pure form from a source of brain tissue comprises the sequence of steps of:
(a) extraction from the source tissue;
(b) cation-exchange chromatography;
(c) heparin affinity chromatography;
(d) cation-exchange chromatography; and, optionally,
(e) hydrophobic-interaction chromatography.

The extraction is accomplished by treating the tissue sequentially with 0.15M ammonium sulfate, adjusting to pH 4.5 with hydrochloric acid, stirring and centrifugation, treating with ammonium sulfate after the pH is adjusted to 6-6.5 with sodium hydroxide, stirring and centrifugation, followed by dialysis and centrifugation.

The first cation-exchange chromatography step comprises batch adsorption on a carboxymethyl-Sephadex column, followed by washing with 100 mM sodium phosphate buffer at pH 6 and elution with 100 mM sodium phosphate, pH 6.0/0.6M NaCl.

The heparin affinity chromatography is performed on a heparin-Sepharose (Pharmacia) column by washing with a buffer containing 10 mM Tris-HCl, pH 7.0/0 6M NaCl, followed by elution with a linear gradient of from 0.6 to 2.0M NaCl in 10 mM Tris-HCl, pH 7.0.

The second cation-exchange chromatography step is performed on a Mono-S (Pharmacia) column equilibrated and, after loading of the sample, washed with 50 mM sodium phosphate, pH 6.8, followed by elution of HBBMs with a linear gradient of from 0 to 0.6M NaCl in 50mM sodium phosphate, pH 6.8.

The hydrophobic-interaction chromatography step comprises preequilibrating a HIC column (LKB Ultropac-TSK-Phenyl-5PW) with a buffer of 100 mM sodium phosphate, pH 7.0, and 1.5M sodium sulfate, followed by elution with a linear gradient of from 1.5 to 0.6M sodium sulfate.

Although the HBBMs may be separated easily and quantitatively from the FGFs by reverse-phase HPLC, this procedure reduces the biological activity of the FGFs due to the conditions used in reverse-phase HPLC. Therefore, in order to separate and isolate the HBBMs and the FGFs in biologically active form for comparative testing, the process set forth above was developed. The use of reverse-phase HPLC was limited to the testing of small aliquots of fractions from heparin-Sepharose affinity chromatography and cation-exchange chromatography for the presence of HBBMs and FGFs. The reverse-phase HPLC steps were performed on a C4 column (The Separations Group) eluted with a shallow gradient of acetonitrile in 0.1% trifluoroacetic acid.

The biological activity of the HBBMs has been established by tests evidencing the induction of mitogenesis in endothelial cells. Although HBBM-2 was not tested, the activity demonstrated for HBBM-1 and HBBM-3 suggests that HBBM-2 will also possess this activity. The testing was performed on bovine aortic arch endothelial cells.

Three separate tests were performed, both to confirm the existence of mitogenic activity and to demonstrate that the activity was due to the HBBMs and not to the FGFs.

Figure 5:
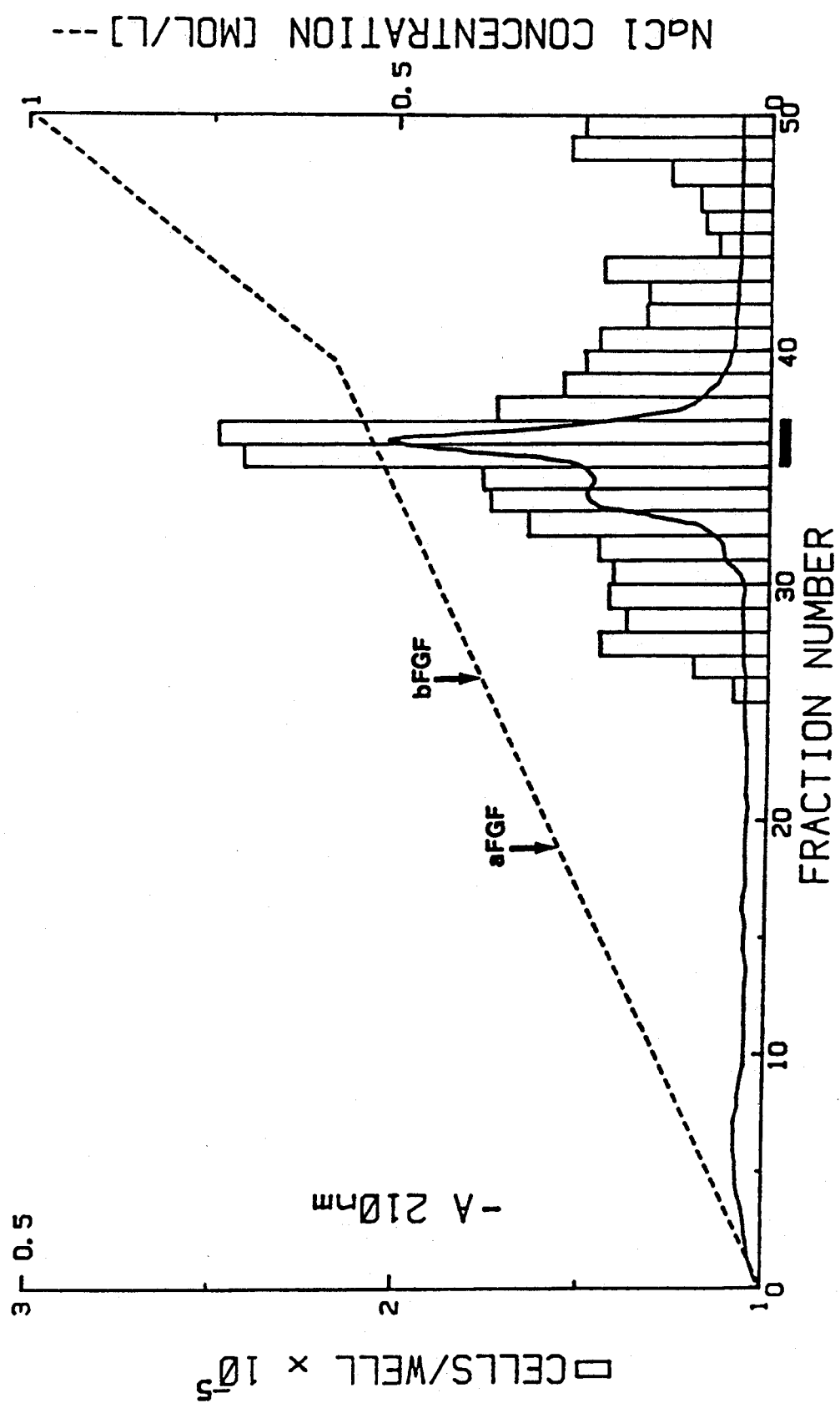
FIG. 5 depicts the rechromatography of HBBM-3 on a Mono-S cation-exchange column. The fractions containing HBBM-3 from the chromatography depicted in FIG. 2 were pooled, diluted three times with starting buffer, and the diluted samples chromatographed on a Mono-S column, under conditions identical to those shown in FIG. 2. Aliquots of fractions were tested for their ability to stimulate the growth of bovine aortic arch endothelial cells (histogram). Retention times of aFGF and bFGF are shown with arrows. A horizontal bar marks the fractions which thereafter were used for concentrating HBBM-3.

First, the eluent fractions from Mono-S chromatography which contained HBBM-3 were pooled, rechromatographed on a Mono-S column and then tested for their ability to stimulate the growth of bovine vascular endothelial cells. For comparison, samples of aFGF and bFGF were also tested. FIG. 5 presents the results of this test.

Figure 6:
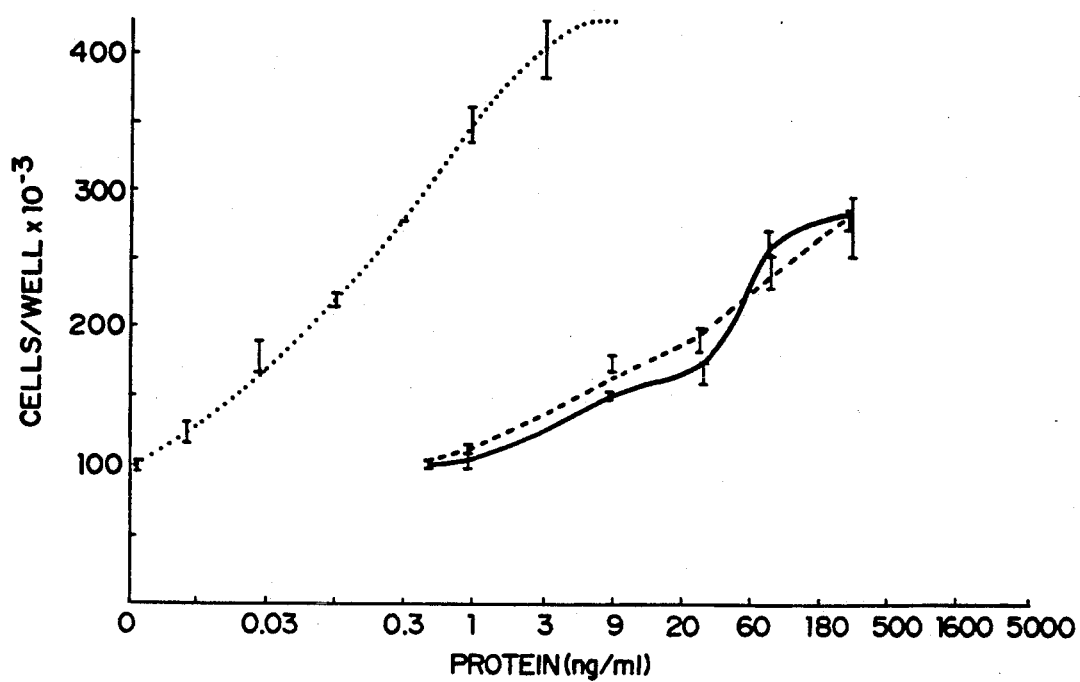
FIG. 6 depicts the biological activity of HBBM-3 and HBBM-1 by means of dose response analysis and comparison with FGF activity. The ability of HBBM-3 and HBBM-1 to stimulate the growth of bovine aortic arch endothelial cells was tested. Upper panel: HBBM-3; Lower panel: HBBM-1. In each panel, solid line: HBBM; dashed line: aFGF; dotted line: bFGF.
Figure 6:
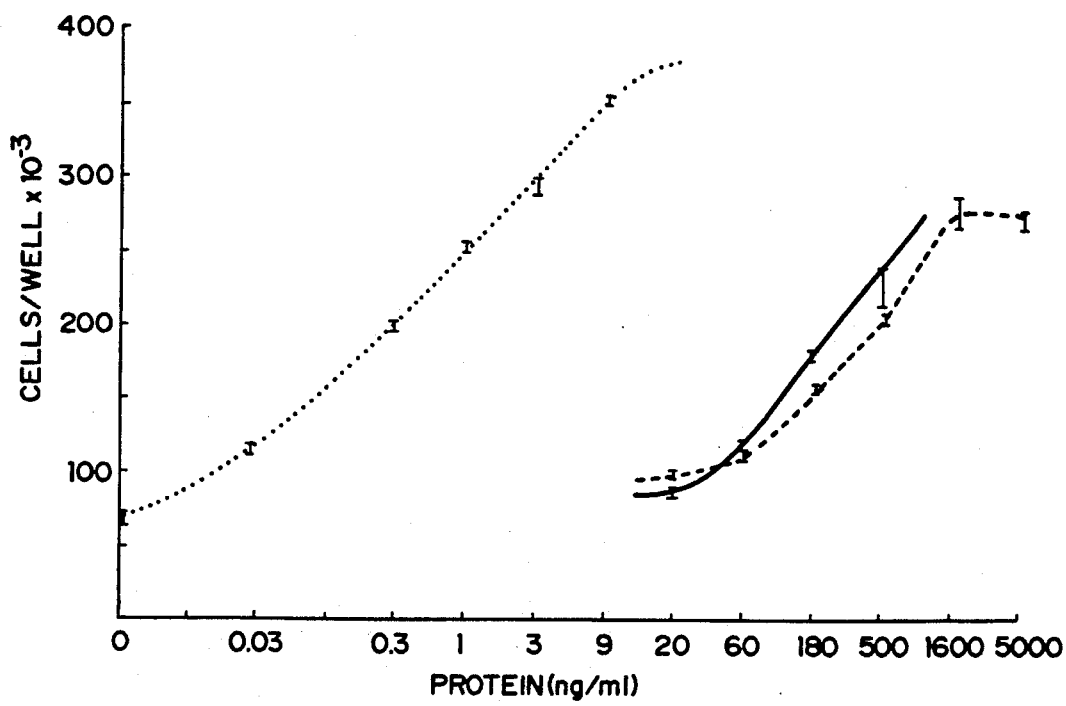

Next, the available HBBM-3 fractions were rechromatographed for sample concentration on a Mono-S column using a steeper gradient and lower flow rate. The HBBM-3 was then compared with aFGF and bFGF in dose-response analyses. The upper panel of FIG. 6 presents the results of this test. This procedure was then repeated for HBBM-1. Those results are presented in the lower panel of FIG. 6.

Figure 7:
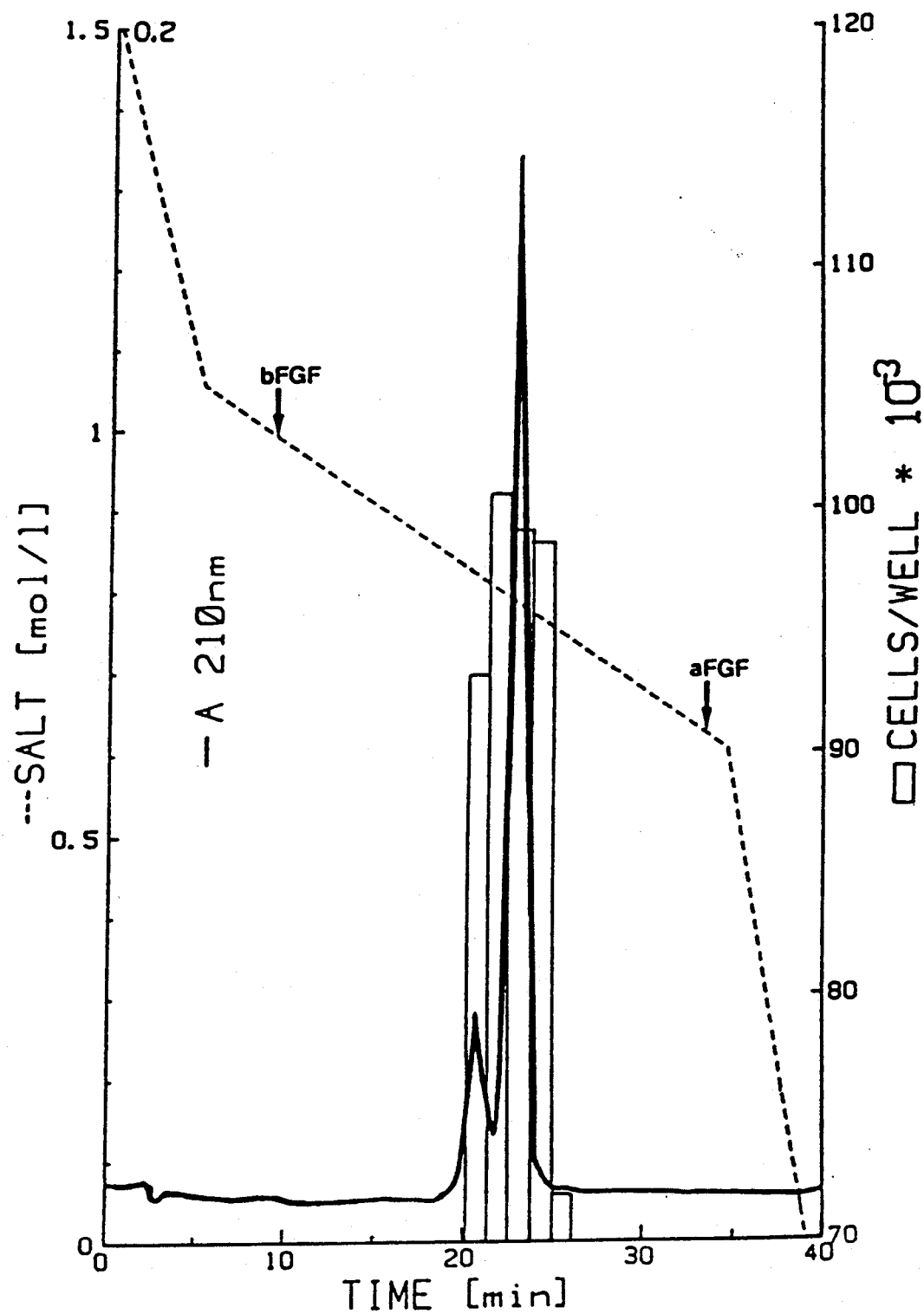
FIG. 7 depicts the chromatography of HBBM-3 on an hydrophobic interaction column. An aliquot of Mono-S-concentrated HBBM-3 was subjected to HIC chromatography. Arrows indicate the retention times of aFGF and bFGF under identical chromatographic conditions. Aliquots of column fractions were tested for their ability to stimulate bovine aortic arch endothelial cell proliferation. The results are indicated by the number of cells grown in each test well.

Finally, HBBM-3 fractions concentrated by Mono-S chromatography were placed on an hydrophobic interaction column, which has different selectivities than a Mono-S column. FIG. 7 presents the results of this test.

These tests established that the HBBMs stimulate the proliferation of cultured bovine vascular endothelial cells in a dose-dependent manner. The $ED_{50}$ was approximately 20 ng/ml for HBBM-3 and 180 ng/ml for HBBM-1. The $ED_{50}$ was calculated as follows: $ED_{50}$=conc [cell no.(dose=0)+cell no.(dose=max)/2].

These mitogens were comparable to the FGFs in terms of biological activity and high affinity to heparin. HBBM-1 and HBBM-3 are each equipotent to aFGF. The $ED_{50}$ are in the range of 50–150 ng/ml.

The test results also make plain that the biological activity associated with HBBM-3 was genuine and was not the result of contamination with an FGF. HBBM-3 and the FGFs are clearly separated by highly resolutive Mono-S chromatography, as shown in FIG. 5, and are also clearly separated by a second high resolution technique with different selectivities, hydrophobic interaction chromatography, as shown in FIG. 7.

Moreover, the HBBMs did not contain measurable quantities of aFGF as determined by quantitative reverse-phase HPLC. As further evidence that the activity was due to HBBMs, the HBBMs were not cross-reactive in an immuno-dot assay using polyclonal antibodies raised against synthetic peptides corresponding to the N-terminal 15 residues of aFGF (1-15) and bFGF (30-50), the latter yielding an antibody which cross-reacts with aFGF (antibodies provided by A. Baird, Salk Institute; growth factor nomenclature according to refs. 5,7). Finally, the concentrations of HBBM and aFGF preparations were carefully determined by quantitative amino acid analysis as a basis for potency comparisons (FIG. 6). Based on those measurements, an inherently inactive HBBM-3 would have to be contaminated with an equal amount of aFGF in order to produce the biological response seen. The results rule out such a contamination. In summary, the results of those studies clearly show that the activity of HBBM-3 is not a consequence of aFGF contamination.

Several lines of evidence indicate, furthermore, that HBBM-3 activity is not due to bFGF contamination. In theory, a few percent contamination of HBBM-3 with bFGF would suffice to produce the activities observed. However, such a contamination is not indicated, because HBBMs and bFGF are widely separated on heparinSepharose chromatography. Moreover, HBBM-3 and bFGF are also well-separated in Mono-S chromatography (FIG. 5). Finally, when HBBM-3 was subjected to chromatography on a third highly resolutive system, hydrophobic interaction chromatography, it was evident that biological activity was still associated with HBBM-3 and not with the well-separated bFGFs (FIG. 7). There is no evidence that the two entities would copurify, even in trace amounts, in three widely disparate and resolutive chromatographic systems.

Based on those results, it is concluded that the activity of HBBM-3 is genuine and not the result of contamination with the known heparin-binding FGFs.

The HBBMs are further distinguished from the FGFs by a lack of amino acid sequence homology between the two groups of proteins. In addition to the difference in N-terminal sequences described earlier, the presently available sequence information (approximately 75 of 130 residues of HBBM-3) shows no sequence homology to the published 146 residue sequence of the FGFs (5).

The mitogenic activity of human HBBMs was generally found to be indistinguishable from that of bovine HBBM, although the human mitogens were less extensively characterized owing to limited quantities of material available. This is consistent with other findings: identical amino-terminal sequence, presence of three forms, and retention behavior on ion-exchange, heparin-Sepharose, and reverse-phase chromatography.

The identity of N-terminal sequences among the various sources of the HBBMs suggests that evolutionary pressure may have prevented mutations, at least during the evolution from birds to mammals. Sequence conservation as a result of evolutionary pressure is strongly suspected with many well-known, biologically active proteins that are highly homologous between species.

The HBBMs were not present in bovine kidney tissue that was extracted using the procedure for brain tissue Therefore, the HBBMs are novel proteins which may also play a role in the formation, maintenance and/or repair of tissue, in particular, neural tissue.

The bases for this statement about the role of HBBMs are the following: (1) the HBBMs have the same biological and heparin-binding activities as aFGF; (2) the HBBMs are brain-specific; (3) higher amounts of the HBBMs than aFGF are found in the brain; and (4) aFGF and bFGF are known to have very prominent neural activities, such as neurotrophic (neuron survival) activity in vivo and in vitro, they are mitogenic for neuroblasts and glial cells, they promote neurite outgrowth and induce brain-specific protein synthesis.

Although the protein structures of the HBBMs and the FGFs are dissimilar, their similarity in terms of heparin binding and biological activity suggests that both groups of mitogens act through a similar mechanism. For example, the mitogens could bind to cell surface or extracellular, matrix-associated heparinlike structures.

Therapeutic compositions in accordance with this invention include HBBMs, either singly or in mixtures, dispersed in a conventional pharmaceutically acceptable liquid or solid carrier. The therapeutic compositiohs may be administered topically in the form of creams, lotions and so forth, or orally in such forms as tablets, capsules, dispersible powders, granules or suspensions, or parenterally in the form of sterile injectable solutions or suspensions. These therapeutic compositions may be administered to human or veterinary patients to promote angiogenesis and the repair and maintenance of neural tissue.

EXAMPLE

In this example, the isolation and characterization of bovine HBBM are set forth in detail. Results using human material were very similar and will not be described in detail unless differences from bovine material were found.

1) Tissue Extraction

Human brains were obtained less than 24 hours postmortem from the Department of Pathology, University of Zurich. Bovine brains were obtained at a slaughterhouse. Tissues were frozen immediately after receipt, stored at −80° C., and processed within two weeks after receipt. Batches of 3-5 kg of brain tissue were extracted at a time.

Brain tissue was extracted following the procedure developed by Gospodarowicz and co-workers (2) as described (6,10): Frozen brains were crushed with a hammer. Six-hundred gram portions of tissue were homogenized in 1.2 1 of 0.15M ammonium sulfate for 3 minutes in a Waring Blender. The pH of the homogenate was adjusted immediately to pH 4.5 with concentrated HCl and the mixture was further homogenized using a Polyton homogenizer until the tissue was finely dispersed. The homogenate was then extracted by stirring of the suspension for 2 hours at 4° C. followed by centrifugation at 4° C. for 60 minutes at either 11,500 rpm (GSA rotor) or 9,000 rpm (GS-3 rotor) to remove cells and debris. The supernatant was adjusted to pH 6-6.5 with NaOH, ammonium sulfate (230 g/l) was added slowly, and the resulting suspension was stirred for at least 30 minutes at 4° C. and centrifuged again as described above. The pellet was discarded. More ammonium sulfate (300 g/l) was slowly added to the supernatant, the suspension was stirred for at least 30 minutes at 4° C. and centrifuged as above. The resulting pellet was dissolved in cold water (100 ml per kg of starting material) and dialysed at 4° C. for 20 hours against 20 l of water using a Spectrapor membrane (molecular weight cut-off 6-8 kD, diameter 31.8 mm). The dialysate was centrifuged again to remove precipitated material and the supernatant subjected to chromatographic purification (see below) after determining its conductivity.

2) Cation Exchange Chromatography

The tissue extract resulting from the above procedure (approximately 150 ml for each kg of brain tissue) was subjected to batch adsorption/elution by cation exchange chromatography as follows: The sample was diluted with water as required to bring the conductivity below that of a 0.1M sodium phosphate buffer (pH 6)/0.15M NaCl solution. The sample was then loaded onto a column of carboxymethyl-Sephadex (5.5×3 cm) which was preequilibrated with 100 mM sodium phosphate (pH 6)/0.15M Cl. The column was washed with the equilibration buffer and a protein fraction was eluted with 100 mM sodium phosphate, pH 6.0/0.6M NaCl and collected. All operations were carried out at room temperature and a flow rate of 500 ml/hour.

3) Heparin-Sepharose Affinity Chromatography

The 0.6M NaCl eluate from cation exchange chromatography was loaded on a heparin-Sepharose column (Pharmacia, 5×1.5 cm) at a flow rate of 125 ml/hour. The column was washed with 200 ml of a buffer containing 10 mM Tris-HCl, pH 7.0/0.6M NaCl until the absorbance of the column eluate at 280 nm became negligible. Protein bound to the column was eluted with a 120-minute linear gradient from 0.6M to 2M NaCl in 10 mM Tris-HCl, pH 7.0 at a flow rate of 35 ml/h. Chromatography was performed at room temperature using a LKB peristaltic pump and a low pressure LKB programmable gradient former. Fractions of 1.4 ml were collected and aliquots subjected to bioassay.

The results of this Heparin-Sepharose chromatography are shown in FIG. 1. The fractions subjected to further purification, using steps described below, are indicated by the horizontal bar A. The fractions containing aFGF eluted between 1.1-1.3M NaCl (as determined by HPLC analysis of individual heparin-Sepharose column fractions; data not shown) and correspond to the shoulder of the larger peak eluting at 1-1.2M NaCl, and to the horizontal bar B. The reverse-phase HPLC analysis was conducted on a C4 column (25×0.46 cm, 5 um particle size, 300 angstroms pore size, The Separations Group, Hesperia, Calif.). The proteins were eluted in a shallow gradient of acetonitrile (10%/hour) in 0.1% trifluoroacetic acid at a flow rate of 0.7 ml/minute. The heparin-Sepharose chromatography was performed at room temperature.

4) Mono-S Cation Exchange Chromatography

In order to separate the contaminating aFGF from the other protein material, fractions eluting at 1-1.2M NaCl were pooled, diluted sufficiently with a buffer containing 50 mM sodium phosphate, pH 6.8 (to reduce their ionic strength to approximately that of the diluent) and subjected to cation-exchange chromatography on a Mono-S column (Pharmacia) equilibrated with 50 mM sodium phosphate, pH 6.8. This material was pumped onto a Mono-S column (Pharmacia) equilibrated with 50 mM sodium phosphate, pH 6.8. After washing the column with the same buffer until the absorbance at 210 nm reached a minimum value, protein was eluted with a gradient from 0 to 0.6M NaCl in 50 mM sodium phosphate, pH 6.8.

Figure 2:
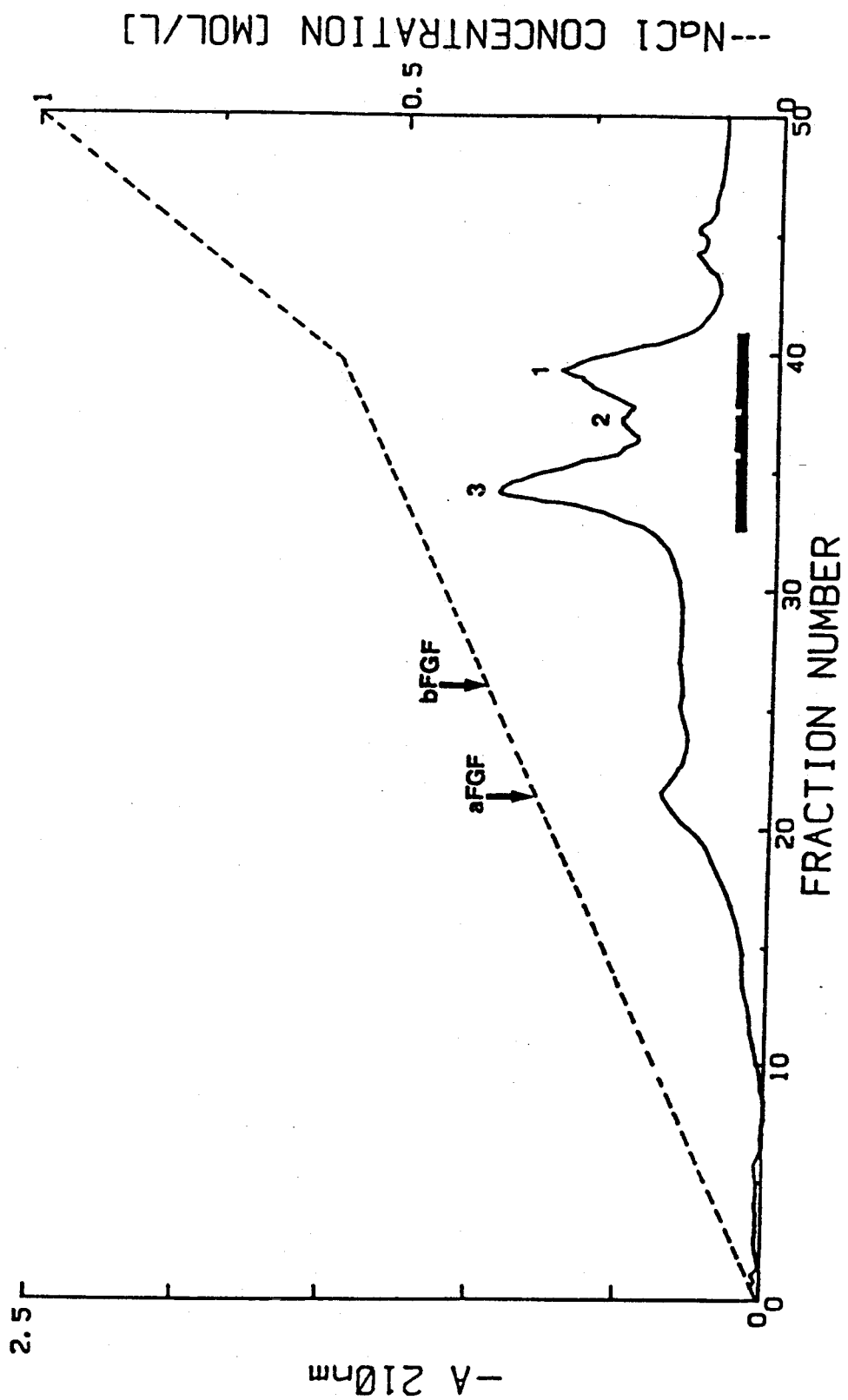
FIG. 2 depicts the results of Mono-S cation exchange chromatography on 20 ml of the material eluted from the heparin-Sepharose affinity chromatography (as indicated by the horizontal bar A, FIG. 1). Arrows indicate the elution positions of aFGF and bFGF standards. The numbers in the chromatogram refer to HBBM-1, -2, and -3. The horizontal bar indicates the fractions containing the HBBMs which were used as a pool or individually for further purification/characterization.

Several well-discernible peaks were eluted from the Mono-S column under these conditions, as shown in FIG. 2. Each peak was analyzed by reverse-phase HPLC using LKB HPLC equipment at room temperature with a flow rate of 0.7 ml/minute.

The first and quantitatively minor peak which eluted from the Mono-S column at 0.3M NaCl corresponded to aFGF as evidenced by co-elution with a reference standard of authentic aFGF in the same system under identical conditions (see arrow in FIG. 2), as well as by co-elution in reverse-phase HPLC on a previously-described C4 column, eluted under highly resolutive, shallow gradient conditions (data not shown). The presence of aFGF in this Mono-S column fraction was expected, because the originating fraction from heparin-Sepharose chromatography is known to contain aFGF. The major part of the material eluted from the Mono-S column at approximately 0.45-0.65M NaCl as a relatively well-resolved triplet of peaks. Since those peaks were determined to contain HBBM, as hereinafter described, they were designated as HBBM-3, HBBM-2, and HBBM-1, in the order of their elution (FIG. 2). The elution behavior of human HBBM on a Mono-S column is similar in general, but has been less well studied than bovine HBBM.

The HBBMs are clearly distinguishable by chromatographic retention not only from aFGF but also bFGF (FIG. 2).

Figure 3:
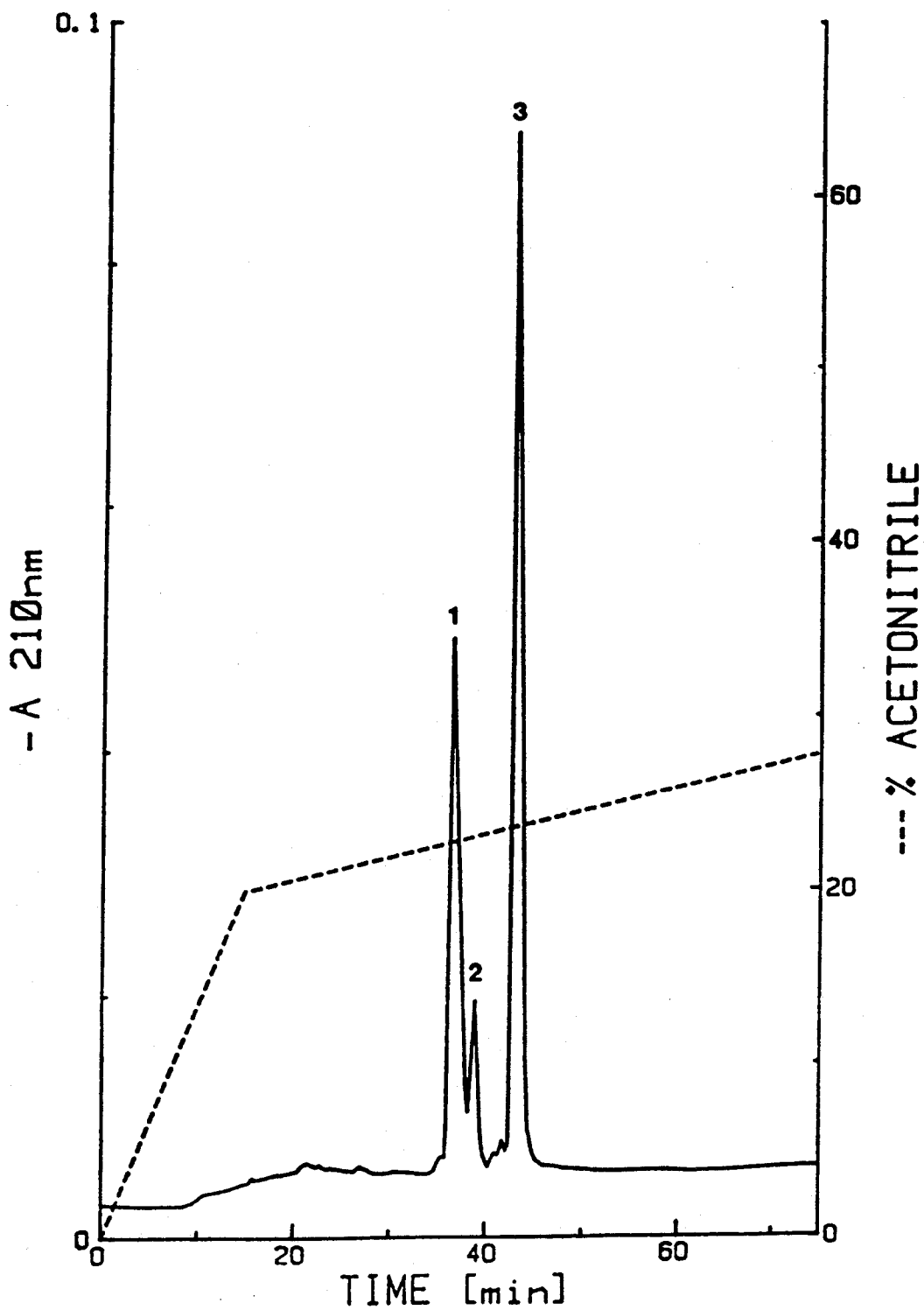
FIG. 3 depicts the reverse-phase HPLC of HBBMs. An aliquot of the pool of Mono-S-purified HBBMs (peaks 1-3, as indicated by the horizontal bar in FIG. 2) was subjected to reverse-phase HPLC. Individual peaks were identified and assigned to specific Mono-S fractions by analyzing aliquots of Mono-S chromatography fractions (as indicated by sections of the horizontal bar in FIG. 2) in independent reverse-phase HPLC runs. Peaks 1-3 refer to HBBM-1, HBBM-2, and HBBM-3, respectively.

Moreover, when analyzed by reverse-phase HPLC (FIG. 3), the HBBMs were also found to differ clearly from the FGFs with respect to retention times (data not shown). Finally, reverse-phase HPLC separated all three HBBMs from each other (FIG. 3) and thus provided a means for their preparation in high purity (as needed for structural characterization) and for relatively unambiguous identification.

Human brain also yielded three forms of HBBMs with reverse-phase HPLC elution patterns identical to those of their bovine counterparts.

5) Hydrophobic Interaction Chromatography

Fractions from Mono-S chromatography containing samples of interest were made 1.5M in sodium sulfate and applied to an HIC column (LKB Ultropac TSK-Phenyl-5PW, 7.5×75 mm) which was preequilibrated with a buffer of 100 mM sodium phosphate, pH 7.0/1.5M sodium sulfate. Protein was chromatographed at room temperature using a 30-minute linear gradient from 1.5 to 0.6M sodium sulfate at a flow rate of 1.0 ml/min. Hydrophobic interaction chromatography is a separation system with selectivities quite different from Mono-S chromatography. Consequently, the separation of the HBBMs from the FGFs by HIC (as shown in FIG. 7), reinforces the result of Mono-S chromatography (as shown in FIG. 5) that the HBBMs are different chemical entities from the FGFs.

6) Amino Acid N-Terminal Sequence Analysis

Usually, sequence analyses were conducted without chemical modification of the proteins. However, as a preliminary step in conducting some analyses of the amino acid N-terminal sequence of the HBBMs, the cysteine residues of the HPLC-purified proteins were treated according to the procedure of Gautschi-Sova et al. (6). Briefly, the cysteine residues were reduced with a five-fold molar excess of dithiothreitol and alkylated by carboxymethylation using a three-fold molar excess of iodo-[2-$^{14}$C]-acetic acid.

The amino acid N-terminal sequence analyses of proteins (100-500 pmol) were performed on an Applied Biosystems (Foster City, Calif.) Model 470A gas/liquid phase protein microsequenator as described by Esch et al. (5). In addition, phenylthiohydantoin (PTH) derivatives of amino acids were identified by reverse-phase HPLC on an Applied Biosystems Model 120A On-line PTH amino acid analyzer. Both procedures were carried out according to protocols from the instrument manufacturer using chemicals supplied by Applied Biosystems.

The N-terminal sequences of all three HBBMs were found to be identical to each other for the first 19 amino acids. The sequences were determined as Gly-Lys-Lys-Glu-Lys-Pro-Glu-Lys-Lys-Val-Lys-Lys-Ser-Asp-Cys-Gly-Glu-Trp-Gln. Human HBBMs (probably analyzed as a mixture) were found to possess the same N-terminal sequence as bovine HBBMs.

While sequencing data clearly indicate that the three bovine HBBM proteins are structurally related to each other, amino acid compositions and molecular weights further suggest that those proteins may differ in the carboxy-terminal region. All data are compatible with the alternative interpretations that either HBBM-2 and HBBM-3 are carboxy-terminally truncated forms of HBBM-1, lacking approximately 13 and 29 amino acids, respectively, at their carboxy-terminals.

7) Molecular Weights of HBBMs

Figure 4:
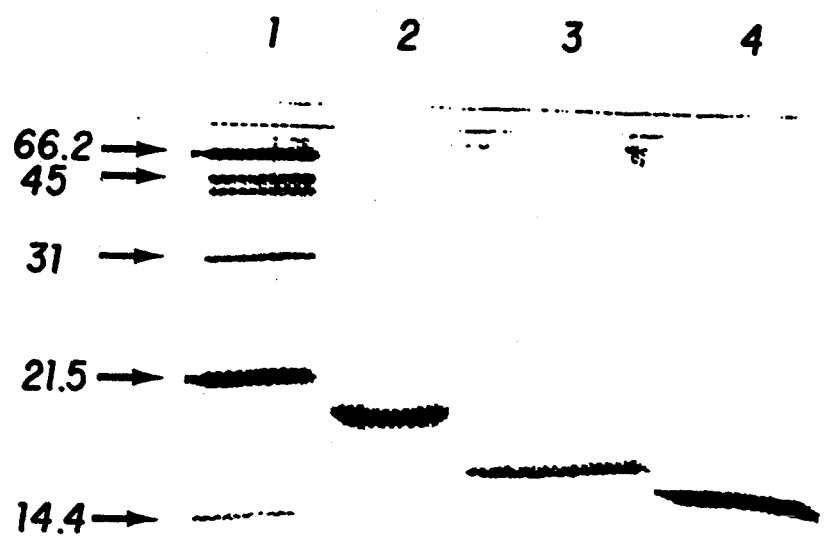
FIG. 4 depicts the analysis on SDS-PAGE of the HBBMs as follows: Lane 1: Protein standards (lysozyme, 14.4 kD; trypsin inhibitor, 21.5 kD; carbonic anhydrase, 31 kD; ovalbumin, 45 kD; serum albumin, 66.2 kD); Lane 2: HBBM-1; Lane 3: HBBM-2; Lane 4: HBBM-3.

Protein samples were analyzed using sodium dodecyl sulfate polyacrylamide gel electrophoresis ("SDS-PAGE") as described by Gospodarowicz et al. (9). Briefly, molecular weight determinations were performed by SDS-PAGE as follows: Aliquots containing 40-80 ng of protein were added to the sample buffer composed of 30% (v/v) glycerol, 0.2M dithiothreitol, 4% (w/v) sodium dodecyl sulfate, 4 mM EDTA, and 75 mM Tris-HCl, pH 6.8. Samples were boiled for 3 minutes and then applied to a 20% polyacrylamide gel slab (1.5 mm) with a 3% stacking gel. Electrophoresis under non-reducing conditions was performed in identical fashion except that dithiothreitol was omitted from the sample buffer. A protein standard mixture containing lysozyme (14.4kD), trypsin inhibitor (21.5kD), carbonic anhydrase (31 kD), ovalbumin (45 kD) and serum albumin (66.2 kD) was also applied to each gel. SDSPAGE revealed the molecular weights of HBBM 1, -2, and -3 to be 18, 16 and 15 kD, respectively (FIG. 4). The molecular weights did not differ significantly regardless of whether the samples were electrophoresed in the presence or absence of reducing agent, indicating that the proteins are single chain polymers. The molecular weights of the human HBBMs have not yet been determined by SDS-PAGE.

8) Amino Acid Composition Analysis

A 10-20 pmol protein sample was hydrolyzed according to the high sensitivity methodology of Bohlen and Schroeder (11). Briefly, the protein sample was added to a hydrolysis tube and dried in vacuo. Fifty µl constant boiling HCl containing 2% (v/v) thioglycollic acid were added. The tube was then evacuated with high vacuum (less than 50mm Torr) after freezing the sample in liquid nitrogen. The sample was then allowed to melt while under vacuum and the tube was flame-sealed.

The tube was hydrolyzed by heating at 110° C. for 20 hours. After hydrolysis, the tube was opened, dried in vacuo, and the residue dissolved in 130 µl citrate buffer (0.067 sodium citrate, pH 2.20) prior to loading on the cation exchange chromatography column.

The protein hydrolysates were chromatographed on a Chromakon 500 amino acid analyzer (Kontron, Zurich, Switzerland) equipped with a polystyrene-based cation exchange column and an o-phthalaldehyde fluorescence detection system for high-sensitivity detection (11).

Quantitation of amino acids was by the external standard method using an amino acid standard mixture. Based on quantitative amino acid analysis, the overall isolation yield of HBBMs was estimated at approximately 30, 10, and 40 µg/kg brain tissue for HBBM-1, HBBM-2, and HBBM-3, respectively.

Amino acid compositions of the three HPLC-purified proteins are shown in Table I.

TABLE I

| Amino acid compositions of heparin-binding brain mitogens | | | |
|---|---|---|---|
| | HBBM-1 | HBBM-2 | HBBM-3 |
| Molecular weight[1] | 18,000 | 16,000 | 15,000 |
| Order of elution | | | |
| reverse-phase HPLC | 1 | 2 | 3 |
| Mono-S | 3 | 2 | 1 |
| Amino acid (number of residues) | | | |
| Asparagine & aspartic acid | 10 | 10 | 9 |
| Threonine | 14 | 14 | 13 |
| Serine | 9 | 9 | 6 |
| Glutamine & glutamic acid | 23 | 20 | 17 |
| Proline | nd[2] | nd | nd |
| Glycine | 16 | 15 | 13 |
| Alanine | 10 | 8 | 8 |
| Cysteine | nd | nd | nd |
| Valine | 4 | 4 | 4 |
| Methionine | 1 | 1 | 1 |
| Isoleucine | 2 | 2 | 2 |
| Leucine | 8 | 7[3] | 8 |
| Tyrosine | 2 | 2 | 1 |
| Phenylalanine | 2 | 2 | 2 |
| Histidine | 1 | 1 | 1 |
| Lysine | 35 | 28 | 23 |
| Tryptophan | 3 | nd[3] | 3 |
| Arginine | 8 | 7[3] | 8 |

[1]as determined by SDS-PAGE
[2]nd: not determined
[3]in accordance with the hypothesis of C-terminal truncation, it is believed that the following are the proper values for HBBM-2: Leucine 8, Tryptophan 3, Arginine 8.

Amino acid compositions are calculated from 3-5 determinations.

Amino acid compositional data agree with the elution order of the three proteins on Mono-S: the least basic protein (HBBM-3) elutes first, while the most basic protein (HBBM-1) elutes last. Expected molecular weights calculated from amino acid analyses are somewhat lower than those determined by SDS-PAGE. The discrepancies may be accounted for by proline and cysteine residues which were not quantitated by amino acid analysis. However, based on the N-terminal sequence analysis, it is known that proline and cysteine are in fact present. Amino acid analyses of human HBBMs are not yet available.

9) Biological Activity

The ability of certain of the HBBMs to induce mitogenesis in endothelial cells was tested by measuring the effect of those proteins on the proliferation in vitro of bovine aortic arch endothelial cells which had been cultured as described by Bohlen et al. (2,10). Briefly, the bovine endothelial cells were seeded with column fractions obtained as described below at low density (10,000-20,000 cells/35 mm dish) in Dulbecco's modified Eagle's medium containing 10% calf serum (Hyclone, Sterile Systems, Logan, Utah). Cultures were grown for 5 days in the presence of various concentrations of column fraction aliquots (added on days 0 and 2) and then counted in a Coulter particle counter. The biological activities of the proteins tested are indicated in the number of vascular endothelial cells grown in each test well for each fraction in FIGS. 5-7.

In particular, activity of the HBBMs was compared with that of the FGFs. Using published procedures (9,12), aFGF and bFGF were isolated and their authenticity was verified by N-terminal sequence analysis and molecular weight determination (SDS-PAGE).

The eluant fractions corresponding to the peak for HBBM-3 from Mono-S chromatography, as shown in FIG. 2, were pooled, diluted three times with starting buffer and rechromatographed on the same system. Aliquots of these fractions were tested as described above for their ability to stimulate the growth of bovine vascular endothelial cells. Comparative tests were run with aFGF and bFGF. The results, as shown in FIG. 5, indicated that HBBM-3 stimulated mitogenic activity for bovine endothelial cells. Furthermore, the HBBM-3 and its activity were separable from the FGFs.

In further test of activity, the available HBBM-3 fractions were concentrated on a Mono-S column using the same buffer system as described for FIG. 2, but with a steeper gradient (0-1.0M NaCl in 20 minutes) and lower flow rate (0.4 ml/minute). Comparative dose-response analyses were run with aFGF and bFGF.

The upper panel of FIG. 6 indicates that HBBM-3 stimulated bovine aortic endothelial cells in a dose-dependent manner. The $ED_{50}$ was in the order of 20-50 ng/ml, with the minimally stimulating dose being approximately 3 ng/ml. The dose-response curves of HBBM-3 and aFGF were indistinguishable, both qualitatively and quantitatively, under the assay conditions used. The response of HBBM-3 appeared to be distinguishable from that of bFGF. In the assay system used, bFGF possessed much higher potency and apparently higher intrinsic activity than HBBM-3. It should be cautioned, however, that the question of intrinsic activity of HBBM-3 could not be addressed adequately in this test because doses sufficiently high to allow assessment of the intrinsic activity of HBBM-3 could not be used in the assay due to limitations with respect to the amount of salt that could be added to the cells without adverse effects on cell growth. Preliminary results indicate, however, that the intrinsic activity of HBBM-3 is identical to that of aFGF under the assay conditions used.

The dose-response analysis was repeated for HBBM-1. The results, as shown in the lower panel of FIG. 6, indicate that HBBM-1 was also biologically active in the same test system. Human HBBM, comprising a mixture of HBBM-1, -2 and -3, was tested in the same manner and was similarly active (data not shown). However, results have not yet been obtained for individual fractions of the human HBBMs. Furthermore, bovine HBBMs were also tested on human umbilical cord endothelial cells and found to be active (data not shown).

Finally, aliquots of HBBM-3 concentrated by Mono-S chromatography were made 1.5M in sodium sulfate and placed on an hydrophobic interaction column. The results, as shown in FIG. 7, indicated that HBBM-3 was active and was well-separated from both aFGF and bFGF.

REFERENCES

1. Gospodarowicz, D., *J. Biol. Chem.*, 250, 2515-2520 (1975).
2. Gospodarowicz, D., Bialecki, H., and Greenburg, G., *J. Biol. Chem.*, 253, 3736-3743 (1978).
3. Bohlen, P., Baird, A., Esch, F., Ling, N., and Gospodarowicz, D., *Proc. Nat. Acad. Sci.*, 81 5364-5368 (1984).
4. Thomas, K., Rios-Candelore, M., and Fitzpatrick, S., *Proc. Nat. Acad. Sci.*, 81, 357-361 (1984).
5. Esch, F., Baird, A., Ling, N., Ueno, N., Hill, F., Denoroy, L., Klepper, R., Gospodarowicz, D., Bohlen, P., and Guillemin, R., *Proc. Nat. Acad. Sci.*, 82, 6507-6511 (1985).
6. Gautschi-Sova, P., Mueller, T., and Bohlen, P. *BBRC*, 140, 874-880 (1986).
7. Gimenez-Gallego, G., Rodkey, J., Bennett, C., Rios-Candelore, M., DiSalvo, J., and Thomas, K., *Science*, 230, 1385-1388 (1985).
8. Bohlen, P., Esch, F., Baird, A., Jones, K., and Gospodarowicz, D., *FEBS Lett.*, 185, 177-181 (1985).
9. Gospodarowicz, D., Cheng, J., Lui, G., Baird, A., and Bohlen, P., *Proc. Nat. Acad. Sci.*, 81, 6963-6967 (1984).
10. Bohlen, P., Esch, F., Baird, A., and Gospodarowicz, D., *EMBO J.*, 4, 1951-1956 (1985).
11. Bohlen, P., and Schroeder, R., *Anal. Biochem.*, 126, 144-152 (1982).
12. Gautschi-Sova, P., Jiang, Z. P., Frater-Schroeder, M., and Bohlen, P., *Biochemistry*, 26, 5844-5847 (1987).

We claim:

1. A method for the isolation of an essentially purified and isolated heparin-binding brain mitogen having the N-terminal amino acid sequence H-Gly-Lys-Lys-Glu-Lys-Pro-Glu-Lys-Lys-Val-, wherein said mitogen is selected from the group consisting of HBBM-1, HBBM-2 and HBBM-3, wherein HBBM-1 has a molecular weight of about 18,000 daltons, HBBM-2 has a molecular weight of about 16,000 daltons and HBBM-3 has a molecular weight of about 15,000 daltons, where said molecular weights are determined by sodium dodecyl sulfate polyacrylamide gel electrophoresis under either reducing or non-reducing conditions, which comprises the sequence of steps of:

(a) extraction from the source tissue to obtain an extract containing the heparin-binding brain mitogen;
   (b) subjecting the extract from step (a) to a first cation-exchange chromatography, such that the eluate contains the heparin-binding brain mitogen;
   (c) subjecting the eluate from step (b) to heparin affinity chromatography, wherein the eluate is added to a heparin affinity column, such that the heparin-binding brain mitogen binds to the column and is then eluted from the column; and
   (d) subjecting the eluate from step (c) to a second cation-exchange chromatography to separate any contaminating acidic fibroblast growth factor from the heparin-binding brain mitogen.

2. The method of claim 1 which further comprises the step of hydrophobic-interaction chromatography after step (d).

3. The method of claim 1 wherein the eluted fractions of steps (c) and (d) are analyzed for the presence of heparin-binding brain mitogen by reverse-phase high performance liquid chromatography.

4. The method of claim 3 wherein the source tissue is bovine brain.

* * * * *